(12) United States Patent
Mattrey

(10) Patent No.: US 6,444,192 B1
(45) Date of Patent: *Sep. 3, 2002

(54) DIAGNOSTIC IMAGING OF LYMPH STRUCTURES

(75) Inventor: Robert F. Mattrey, San Diego, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/245,828

(22) Filed: Feb. 5, 1999

(51) Int. Cl.[7] ............................................... A61B 8/00
(52) U.S. Cl. ...................... 424/9.52; 424/9.5; 600/458
(58) Field of Search ............................. 424/9.52, 9.51, 424/9.5; 600/458, 441

(56) References Cited

U.S. PATENT DOCUMENTS

| | | | |
|---|---|---|---|
| 4,466,442 A | 8/1984 | Hilmann et al. | 128/653 |
| 4,572,203 A | 2/1986 | Feinstein | 128/661 |
| 4,657,756 A | 4/1987 | Rasor et al. | 424/9 |
| 4,675,173 A | 6/1987 | Widder | 424/9 |
| 4,684,479 A | 8/1987 | D'Arrigo | 252/307 |
| 4,718,433 A | 1/1988 | Feinstein | 128/660 |
| 4,844,882 A | 7/1989 | Widder et al. | 424/9 |
| 4,849,210 A | 7/1989 | Widder | 424/9 |
| 4,957,656 A | 9/1990 | Cerny et al. | 252/311 |
| 5,088,499 A | 2/1992 | Unger | 128/662.02 |
| 5,123,414 A | 6/1992 | Unger | 128/654 |
| 5,141,738 A | 8/1992 | Rasor et al. | 424/2 |
| 5,271,928 A | 12/1993 | Schneider et al. | 424/9 |
| 5,315,997 A | 5/1994 | Widder et al. | 128/653.3 |
| 5,393,524 A | 2/1995 | Quay | 424/9 |
| 5,409,688 A | 4/1995 | Quay | 424/9 |
| 5,496,536 A | 3/1996 | Wolf | 424/9.322 |
| 5,498,421 A * | 3/1996 | Grinstaff et al. | 424/450 |
| 5,531,980 A | 7/1996 | Schneider et al. | 424/9.52 |
| 5,536,489 A | 7/1996 | Lohrmann et al. | 424/9.52 |
| 5,540,909 A | 7/1996 | Schutt | 424/9.52 |
| 5,552,133 A | 9/1996 | Lambert et al. | 424/9.52 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,562,893 A | 10/1996 | Lohrmann | 424/9.52 |
| 5,567,413 A | 10/1996 | Klaveness et al. | 424/9.51 |
| 5,573,751 A | 11/1996 | Quay | 424/9.52 |
| 5,578,292 A | 11/1996 | Schneider et al. | 424/9.51 |
| 5,595,723 A | 1/1997 | Quay | 424/9.5 |
| 5,611,344 A * | 3/1997 | Bernstein et al. | 128/662.02 |
| 5,792,475 A * | 8/1998 | Davis et al. | 424/489 |
| 5,837,221 A | 11/1998 | Bernstein et al. | 424/9.52 |
| 5,846,517 A | 12/1998 | Unger | 424/9.52 |
| B1 5,558,094 A | 1/1999 | Quay | 424/9.52 |
| B1 5,573,751 A | 3/1999 | Quay | 424/9.52 |
| 6,205,352 B1 * | 3/2001 | Carroll | 600/431 |

FOREIGN PATENT DOCUMENTS

| | | | |
|---|---|---|---|
| EP | 0 359 246 | 9/1989 | A61K/49/00 |
| WO | WO 96/40282 | 12/1986 | A61K/49/00 |
| WO | WO 91/15999 | 10/1991 | A61B/8/00 |
| WO | WO 95/01187 | 1/1995 | A61K/49/00 |
| WO | WO 96/40278 | 12/1996 | A61K/49/00 |

OTHER PUBLICATIONS

Cotter et al., "Influence of Ultrasonic Energy on Contraste Echocardiography: Intermittent Imaging Using AF0150 Yields Generalized Myocardial Opacification While Continuous Imaging Delineates Intramyocardial Vessels," *Journal of the American College of Cardiology*, 29(2) Supp. A:300A (1997) (abstract—XP000939306).

Cotter et al., "Safety and Efficacy of AFO150 for Cardiac Contrast Enhancement in Normal Subjects: Initial Results of a Phase I Clinical Trial," *Journal of the American College of Cardiology*, 29(2) Supp. A:300A (1997) (abstract—XP-002149781).

Ikomi et al., "Intracellular and Extracellular Transport of Perfluoro Carbon Emulsion from Subcutaneous Tissue to Regional Lymphatics," *Art. Cells, Blood Subs., and Immob. Biotech.*, 22(4):1441–1447 (1994).

(List continued on next page.)

*Primary Examiner*—Michael G. Hartley
(74) *Attorney, Agent, or Firm*—Gray, Cary, Ware & Freidenrich, LLP

(57) ABSTRACT

In accordance with the present invention, there are provided methods for identifying the sentinel lymph node in a drainage field for a tissue or organ in a subject. In select embodiments, the invention allows for the identification of the first or sentinel lymph node that drains the tissue or organ, particularly those tissues associated with neoplastic or infectious diseases and disorders, and within the pertinent lymph drainage basin. Once the drainage basin from the tissue or organ, i.e., the sentinel lymph node, is identified, a pre-operative or intraoperative mapping of the affected lymphatic structure can be carried out with a contrast agent. Identification of the first or sentinel lymph node, on the most direct drainage pathway in the drainage field, can be accomplished by a variety of imaging techniques, including ultrasound, MRI, CT, nuclear and others. Moreover, once the lymphatic structure is identified as being associated with neoplastic or infectious diseases and disorders, the affected lymphatic structure can be removed surgically or by a suitable minimally invasive procedure to allow pathological analysis to be performed to determine whether certain diseases or disorders exist, without resort to more radical lymphadenectomy. Further, the agent can be made to carry diagnostic or therapeutic probes to be activated and/or delivered to the injection site or any part of the lymphatic pathway downstream from the injection site.

15 Claims, No Drawings

OTHER PUBLICATIONS

McIntyre et al., "Pulmonary Delivery of Nanoparticles of Insoluble, Iodinated CT X–ray Contrast Agents to Lung Draining Lymph Nodes in Dogs," *Journal of Pharmaceutical Sciences*, 87(11):1466–1470 (1998).

Ohmori et al., "Relation of contrast echo intensity and flow velocity to the amplification of contrast opacification produced by intermittent ultrasound transmission," *American Heart Journal*, 134(6):1066–1074 (1997).

R. Mattrey, "The Potential Role of Perfluorochemicals (PFCS) in Diagnostic Imaging," *Art. Cells, Blood Subs., and Immob. Biotech.*, 22(2):295–313 (1994).

Taylor et al., "Renal Cortical Perfusion in Rabbits: Visualization with Color Amplitude Imaging and an Experimental Microbubble–based US Contrast Agent," *Radiology*, 201(1):125–129 (1996).

Taylor et al., "Sonographic Ventriculography: A New Potential Use for Sonographic Contrast Agents in Neonatal Hydrocephalus," *American Journal of Neuroradiology*, 19(10):1931–1934 (1998).

Walker et al., "Studies of Bubble Persistence vs Standard and Harmonic Mode Acoustic Pulse Pressure for Three New Echocontrast Agents," *Journal of the American College of Cardiology*, 29(2) Supp. A:300A (1997) (abstract—XP–000939305).

Bergqvist et al., "Particle Sizing and Biokinetics of Interstitial Lymphoscintigrapic Agents," *Seminars in Nuclear Medicine*, 8(1):9–19 (Jan. 1983).

Calliada et al., "Ultrasound contrast agents Basic principles," *European Journal of Radiology*, 27:S157–S160 (1998).

Coburn and Bland, "Surgery for early and minimally invasive breast cancer," *Current Opinion in Oncology*, 7:506–510 (1995).

DeLand et al., "Lymphoscintigraphy with Radionuclide–labeled Antibodies to Carcinoembryonic Antigen," *Cancer Research*, 40:2997–3000 (1980).

Ege and Warbick, "Lymphoscintigraphy: a comparision of $^{99}Tc^m$ antimony sulphide colloid and $^{99}Tc^m$ stannous phytate," *British Journal of Radiology*, 52:124–129 (1979).

Giuliano et al., "Lymphatic Mapping and Sentinel Lymphadenectomy for Breast Cancer," *Annals of Surgery*, 220(3):391–401 (1994).

Kapteijn et al., "Reproducibility of Lymphoscintigraphy for Lymphatic Mapping in Cutaneous Melanoma," *The Journal of Nuclear Medicine*, 37(6):972–975 (1996).

Krag et al., "Sugical resection and radiolocalization of the sentinel lymph node in breast cancer using a gamma probe," *Surgical Oncology*, 2:335–340 (1993).

Maurer et al., "Evaluation of Metastases and Reactive Lymph Nodes in Doppler Sonography Using an Ultrasound Contrast Enhancer," *Investigative Radiology*, 32(8):441–446 (1997).

Morton et al., "Technical Details of Intraoperative Lymphatic Mapping for Early Stage Melanoma," *Arch. Surg.*, 127:392–399 (1992).

Oussoren et al., "Lymphatic uptake and biodistribution of liposomes after subcutaneous injection. II. Influence of liposomal size, lipid composition and lipid dose," *Biochimica et Biophysica Acta*, 1328:261–272 (1997).

Oussoren and Storm, "Lymphatic Uptake and Biodistribution of Liposomes After Subcutaneous Injection: III. Influence of Surface Modification with Poly(ethleneglycol)," *Pharmaceutical Research*, 14(10):1479–1484 (1997).

Petrek and Blackwood, "Axillary Dissection: Current Practice and Technique," *Curr Probl Surg*, 267–323 (1995).

Uren et al., "Mammary Lymphoscintigraphy in Breast Cancer," *J. Nucl. Med.*, 36:1775–1780 (1995).

Vera et al., "Sentinel Node Imaging Via a Nonparticulate Receptor–Binding Radiotracer," *The Journal of Nuclear Medicine*, 38(4):530–535 (1997).

Vogl et al., "Contrast–Enhanced Lymphography," *Acta Radiologica*, 38(Supp 412):47–50 (1997).

\* cited by examiner

DIAGNOSTIC IMAGING OF LYMPH STRUCTURES

FIELD OF THE INVENTION

In a broad aspect, the present invention is directed to methods of imaging lymphocytic structures. More particularly, the present invention advantageously uses contrast agents to identify and image lymphatic ducts, sentinel nodes and/or other lymph nodes by various means, including ultrasound and MRI.

BACKGROUND OF THE INVENTION

The lymphatic system is made of vessels or ducts that begin in tissues and are designed to carry lymph fluid to local lymph nodes where the fluid is filtered and processed and sent to the next lymph node down the line until the fluid reaches the thoracic duct where it enters the blood stream. Lymph vessels infiltrate all tissues and organs of the body. Lymph fluid is generated from capillaries which because of tissue motion and hydrostatic pressure, enters the lymph vessels carrying with it local and foreign substances and materials from the tissues. These local and foreign molecular, micromolecular and macromolecular substances include antigens, infectious agents, particles and cells. Lymph nodes, the lymph "filters", consist of essentially two major compartments: the fluid spaces, or sinuses, and the cellular elements. There is one major sinus at the outer margin of the node that feeds a maze of sinuses that serve to percolate the fluid slowly towards the hilum of the node from where it is carried downstream. The sinuses are lined by macrophages that phagocytose materials carried by the fluid, particularly if the materials have certain surface charges or specific shapes. The remainder of the cellular elements in the lymph node performs the immunologic function of the node. In this regard, the lymph nodes process fluid by sieving and phagocytosis to remove particulate and cell materials delivered by the lymphatic vessels, thereby cleaning it before it is returned to the blood stream.

The local particulate materials carried to the node are typically proteins that either escaped the capillary beds or were produced by tissues or organs. Foreign particulates are micromolecular (less than 1 micrometer) or macromolecular (greater than one micrometer), and include viruses, bacteria, and injectable suspensions such as contrast media or radiopharmaceuticals. The particles enter the lymph vessel from the interstitium through gaps between lymphatic endothelial cells or by transcellular endo-exocytosis. The gaps change in caliber with physiologic or pathologic conditions. Entry of the particle into the gap is believed to be a hit-or-miss affair and should be weakly related to particle size at dimensions less than the size of the gap.

On average, smaller particles (10–50 nm) are more likely to enter than larger particles. As particles approach 1000 nm, their uptake into lymphatics is so poor that they become ineffective. Very large particles in the interstitial space must be carried away by phagocytes or reduced in size by local processes. In fact over 95% of particles larger than 400 nm were found to remain at the injection site (Oussoren et al., Pharm Res. (1997) 4(10):1479–1484 and Oussoren et al., Biochim Biophys Acta. (1997) 1328(2):261–272) whereas 74% of particles 10 times smaller (40 nm) were absorbed. Small particles (less than 5 nm) and particles without appropriate surface characteristics are not retained by the first lymph node and are carried to downstream lymph nodes or directly into the blood stream by the capillaries.

Several attempts have been made to improve retention of diagnostic agents in the lymph node. One is to administer a viscous substance such as ethiodol directly into the lymph vessel thereby plugging the sinuses and hindering the forward progress of the liquid. This technique, called direct lymphangiography, is performed to detect tumor deposits in lymph nodes but is limited to the few regions of the body where direct canulation of the lymph vessel is possible. Another technique is to administer particulate suspensions such as emulsions with specific size distributions that are phagocytosed by macrophages (Wolf et al., U.S. Pat. No. 5,496,536 and Bergquist, et al., Sem. Nucl. Med (1983) 13: 9–19). These agents, although phagocytosed, are not sufficiently retained in the lymph node to halt their progress and highlight several lymph nodes in the local chain. The third technique to promote retention is the placement of surface active substances that promote phagocytosis (Vera et al., J Nucl Med (1997) 38(4):530–5).

The cellular elements carried in lymph or that gain access to lymph nodes are typically the circulating white cells or phagocytes that are involved in the cellular defense mechanism. Although these cells are very large (several tens of micrometers in diameter) they gain access to the lymph space by their ability to deform and migrate through tiny openings. These cells patrol the extracellular space, phagocytose materials and carry such materials into the lymph and the lymph nodes for further action by the immune system. When cancer occurs in tissues or organs, its loose matrix allows the dislodging of cells that gain access to the lymph space. However, because they lack the functionality of white blood cells, they can become trapped in the lymph node and grow. In the early stages of cancer development in the node, the cancer remains limited to the node. However, in time, the nodal deposit can grow to totally replace the node or can spread downstream to the next node. The lymph nodes that drain the tissue or organ of interest (i.e., the cancerous tissue), called the regional nodes, and the first node that traps the cancer is called the sentinel node.

Unfortunately, although certain patterns in the spread of tumors are recognized, these patterns are complicated. Metastasis of neoplastic cells does not simply result in the spread of the neoplastic cells to the next physically nearest node. Nodes in close physical proximity to the primary tumor are more likely to contain the sentinel node, however, the sentinel node may be in a more distant nodal group. This can occur due to normal anatomic pathways that can bypass adjacent nodal clusters. Complex patterns can also arise because tumors, current or prior infections, injury or previous treatments can block the lymph vessels that directly drain the tissue or organ, promoting the development of collateral and aberrant pathways.

Lymphadenectomy is a common procedure that provides local control and staging of breast cancer patients as well as establish prognosis and method of treatment. The degree of involvement of axillary lymph nodes remains the most important prognostic indicator (Cancer 1993:71). These nodes are positive in as many as 40% of breast cancers including those cancers between 5–10 mm in size. Because of the associated morbidity with axillary dissection in as many as 20% of patients (Coburn M C and Bland K I, *Curr Opin Oncol* 1995; 7:506; Petrek J A and Blackwood MM. *Curr Prob Surg* 1995; 267), attempts at limiting dissection have led to the development of sentinel node resection. The concept of the sentinel node dissection was popularized by Morton DL (Arch Surg 1992; 127:392–99) for staging melanoma and Giuliano A E applied it to breast cancer (Ann Surg 1994; 220:391–401). They showed that limiting the dissection to the sentinel node can predict the status of the remainder of the nodal system. When the sentinel node was negative, the remainder of the nodes were negative in 126 out 127 cases. When the node was positive, it was the only positive node in over 60% of cases (Morton DL et al., *Arch Surg* 1992; 127:392) and contained five times more micrometastasis than nonsentinel nodes (Giuliano A E et al., *Ann Surg* 1995; 394). So, in addition to staging, sentinel node resection provides some therapeutic benefit, as all micrometastases would be removed in a majority of cases.

Sentinel lymphadenectomy begins with the injection of 3 to 5 mL of isosulfan blue in the breast mass and surrounding tissue (Giuliano A E et al., *Ann Surg* 1994; 220:391). Approximately 5 minutes later blunt dissection is made to locate a blue lymphatic channel or a blue node. Although all blue nodes are removed, an attempt is made to identify the feeding lymphatic channel, which is then followed proximally toward the breast to ensure the identification of the first and true sentinel node. The resected node(s) is assessed histologically. If the sentinel node is free of disease, dissection is terminated. If the sentinel node is not detected or if it is positive, classic axillary dissection is performed. This technique is much less invasive than lymphadenectomy and is especially useful for patients with low risk for axillary metastasis. Much in this technique bears refinement, however, since Giuliano, the most experienced investigator, reported that the sentinel node was detected in 58% in the first 87 cases and 78% in the next 87 cases.

The failure to identify sentinel nodes results from the fact that they are indistinguishable from breast tissue unless colored blue. Unfortunately, the dye has unpredictable and rapid clearance, and, possibly, the drainage pattern varies. Moreover, as it is water soluble, the blue dye provides a short time-window to identify lymph nodes intraoperatively. Thus, only a few minutes are available between operating too early (where no nodes are stained) or too late (where too many nodes are stained). Yet, other than the blue dye, only radiopharmaceutical agents are available that provide images as they flow through the lymphatic chain (Uren R F et al., *J Nucl Med* 1995; 36:1775; Krag D N et al., *Surg Oncol* 1993; 2:335). Although radiolabelled colloids have a more delayed transit, they are invisible intraoperatively, limiting guidance; they only provide a skin-marking option, and they contaminate the operative field with radioactivity, decreasing the target to background ratio and increasing the complexity of the procedure. Further, only 3 to 4% of the colloid is entrapped, requiring larger dosages than necessary, which flood the field and enhance all nodes, decreasing sentinel node specificity (Ege G N and Warbick A, *Br J Radiol* 1979; 52:124; Kapteijn BAE et al., *J Nucl Med* 1995; 35:222P). At present, most procedures utilize both blue dye and radiolabeled colloids to gain sensitivity. The consequences of failed or difficult sentinel node detection is extensive exploration analogous to or potentially more extensive that the standard lymphadenectomy.

The technique proposed by Wolf et al. (U.S. Pat. No. 5,496,536), indirect lymphography, delivers particle to the tissue or organ to image the draining lymph nodes. However, this technique preferably employs contrast agents that are less than 1 micrometer in diameter. Moreover, it has been reported that such agents are most effective when there is an interval of time between the administration of the contrast agent and imaging for sufficient accumulation of the contrast agent in the nodes (Saunders H B et al., *Radiology.* 1993; 189(P):295). As such, they may complicate normal procedures in the operating room.

Another approach that has been utilized to image the lymph nodes is intravenous administration of suspensions of ultrasmall particles that leak through normal capillaries and become trapped in the lymph nodes by macrophages. Although these agents can visualize nodes, they do not provide any specificity as they visualize all nodes that drain or do not drain a tissue of interest. Therefore, they do not allow the recognition of the sentinel node in the regional nodal chain. Although it is possible to enhance the blood within nodes with intravascular agents to promote the visualization of their intravascular space (not lymphatic space) and aid in the recognition of benign from malignant nodes (Maurer et al., Invest. Radiol. 1997; 32:441), this technique enhances the blood pool in all small lesions whether or not they are in nodes. Moreover, this technique does not permit the recognition of the sentinel node in regional nodes as it enhances the vascular space of all nodes.

Accordingly, there is a need, particularly in oncology, for a method that clearly delineates lymphatic structures employing contrast agents suitable to identify the sentinel lymph node. It would be desirable to further reduce the morbidity of sentinel lymph node biopsy. This would be possible if suitable methodology were available to allow the sentinel lymph node to be identified and removed with as little effect as possible to the surrounding tissue structure. It would be especially desirable to be able to locally administer suitable contrast agents percutaneously and recognize the sentinel node immediately, pre-operatively or intraoperatively, to direct the surgeon to the sentinel lymph node without significant exploration.

SUMMARY OF INVENTION

In a broad aspect, the present invention provides methods and systems for identifying and imaging lymphatic structures in a subject. To this end, the present invention preferably comprises the administration of contrast agents that are preferentially taken up by the lymphatic system and allow for enhanced visualization of the afferent lymphatics and regional lymph nodes. Unlike prior art imaging agents that have been used for such imaging purposes, contrast agents compatible with the present invention are not limited to relatively small particle sizes. Rather, preferred contrast agents of the present invention comprise microbubble preparations having mean bubble sizes on the order of from about one micron to about ten microns. Surprisingly, it has been found that such agents are readily taken up by the lymphatic structures in relatively short order and may easily be detected and imaged using common imaging modalities such as ultrasound or magnetic resonance. Particularly preferred embodiments of the invention will comprise the use of microbubble preparations incorporating an insoluble gas, such as a fluorocarbon, that provides for relatively long half-lives. Those skilled in the art will appreciate that such compositions will preferably be administered interstitially in the region of the lymph node to be imaged.

Significantly, the present invention allows for the identification of the first or sentinel lymph node that drains the tissue or organ of interest, particularly those tissues associated with neoplastic or infectious diseases and disorders, within the pertinent lymph structure. Once the drainage basin from the tissue or organ, i.e., the sentinel lymph node, is identified, a pre-operative or intraoperative mapping of the affected lymphatic structure can be carried out with a contrast agent. Identification of the first or sentinel lymph node, on the most direct drainage pathway in the drainage field, can be accomplished by a variety of imaging techniques, including ultrasound, MRI, CT, nuclear and others. Moreover, once the lymphatic structure is identified as being associated with neoplastic or infectious diseases and disorders, the affected lymphatic structure can be removed surgically or by a suitable minimally invasive procedure to allow pathological analysis to be performed to determine whether certain diseases or disorders exist, without resort to more radical lymphadenectomy.

In yet other aspects the present invention allows for the detection or diagnosis of irregularities associated with one or more components of a lymphatic structure. Further, the contrast agent may be associated with therapeutic or additional diagnostic agents that may be activated and/or delivered to any part of the lymphatic pathway downstream from the injection site. For example, the microbubble preparation could be mixed or associated with an MRI imaging agent such as gadolinium or with a visible dye. The resulting composition could then be imaged using more than one modality (i.e. MRI and ultrasound) or, in the case of dye, could be visually detected during an operative procedure.

Other objects, features and advantages of the present invention will be apparent to those skilled in the art from a consideration of the following detailed description of preferred exemplary embodiments thereof

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated.

As discussed above, the present invention provides improved methods and systems for imaging lymphatic structures in a subject. In this respect, it has suprisingly been found that selected contrast agents, particularly microbubble contrast agents, are especially effective in providing enhanced images of lymphatic structures. Unlike prior art contrast agents and methods that were inconvenient or required relatively small particle sizes, the present invention allows for the use of relatively inexpensive contrast agents having larger particle sizes. Preferably the selected contrast agent will incorporate a plurality of microbubbles comprising a fluorocarbon gas or gas precusor.

Accordingly, in selected embodiments the present invention provides methods for identifying, diagnosing, or treating one or more lymph structures in a subject, said methods comprising:
    administering to said subject a diagnostically effective amount of a particulate contrast agent, said contrast agent typically having a mean particle size in the range of about 1 micron up to about 10 microns in diameter wherein at least a portion of said contrast agent associates with said lymph structure; and
    imaging said subject whereby said lymph structure is detected.

As indicated above, particularly preferred contrast agents for use in the present invention comprise microbubble contrast agents. It will be appreciated that microbubble contrast agents typically comprise a liquid preparation incorporating a plurality of microbubbles. Preferably, microbubble preparations compatible with the present invention will be relatively stable and, in particularly preferred embodiments, will incorporate microbubbles comprising a fluorocarbon gas, vapor or gaseous precursor.

In this regard, the present invention comprises methods for identifying, diagnosing, or treating one or more lymph structures in a subject, said methods comprising:
    administering to said subject a diagnostically effective amount of a microbubble contrast agent, wherein at least a portion of said contrast agent associates with said lymph structure; and
    imaging said subject whereby said lymph structure is detected.

Those skilled in the art will appreciate that the lymph structure preferably comprises a sentinel lymph node. In other embodiments the lymph structure will preferably be downstream from tissue that is neoplastic or suspected of being neoplastic.

Accordingly, another aspect of the present invention provides methods for identifying the sentinel lymph node in a drainage field for a tissue or organ in a subject. The invention is useful for the identification and localization of the sentinel lymph node, the diagnosis of whether the lymph node is normal or affected by disease, which can subsequently lead to resection, treatment and or prevention of lymphatic diseases and disorders (e.g., lymphatic metastases of cancers, lymphomas, lymph node hyperplasia etc.); for differentiation of the above diagnoses; for studying the structure and function of the lymphatic system; for immunomodulation or immunization; for ecological monitoring; and the like.

Thus, a further embodiment of the invention comprises methods for identifying a sentinel lymph node in a subject, said method comprising:
    administering to said subject a diagnostically effective amount of a contrast agent comprising a plurality of microbubbles, wherein at least a portion of said contrast agent associates with said sentinel lymph node; and
    imaging said subject whereby said sentinel lymph node is detected.

It will be appreciated that the identification of the first or sentinel lymph node, on the most direct drainage pathway in the drainage field, can be accomplished by a variety of imaging techniques, including ultrasound, MRI, CT, nuclear and others. Moreover, once the lymphatic structure is identified as being associated with neoplastic or infectious diseases and disorders, the affected lymphatic structure can be removed surgically or by a suitable minimally invasive procedure to allow pathological analysis to be performed to determine whether certain diseases or disorders exist, without resort to more radical lymphadenectomy.

Contrast Agents

As described herein, the invention may be performed with a wide variety of contrast agents using a number of detection procedures. The present invention utilizes contrast agents that have particular characteristics that facilitate their uptake into lymphatics and retention in the regional lymph nodes or the prevention of the their propagation downstream. As used herein, the terms "contrast agent" and "imaging agent" are used interchangeably and broadly encompass any compound, composition or formulation that enhances, contrasts or improves the visualization or detection of an object or system in any way. Exemplary contrast agents include, for example, contrast agents, further described herein, for use in connection with ultrasound, magnetic resonance imaging, X-ray, x-ray computed tomography, nuclear imaging techniques, and the like. Preferred contrast agents will comprise particulate preparations incorporating solid, liquid, or gas particulates. For example, the contrast agent may comprise a suspension or emulsion. Particularly preferred imaging agents comprise microbubble preparations typically used as ultrasound contrast agents.

Those skilled in the art will recognize that a large number of suitable contrast or imaging agents have been described in the literature or are commercially available. As long as they meet the criteria set forth herein, any of these agents are contemplated for use in the disclosed invention.

Contrast agents suitable for imaging by one or more imaging techniques in accordance with the present invention, are preferably in particulate form and are adapted to be preferentially taken up by the lymphatic system upon percutaneous administration. These contrast agents can be radiopaque materials, MRI imaging agents, ultrasound imaging agents, radiopharmaceuticals and any other contrast agent suitable for detection by a device that images an animal body. They are preferably nontoxic, and generally should have an average particle size between about 1 micron and about 20 microns. Of course, in any given particulate system, particle sizes usually form a distribution. Typically, the mean particle sizes fall within the range of about 1–10 microns, preferably within the range of about 2–8 microns.

As used herein, the term "micron" refers to a unit of measure of one one-thousandth of a millimeter or one $\mu$m.

In preferred embodiments of the present invention, contrast agents will be elastic or deformable or capable of being elastic under certain conditions, e.g., temperature, pH, light, application of energy (e.g., ultrasound, and the like), and the like. As employed herein, the term "elastic" refers to the ability of contrast agents employed in the present invention to be non-rigid and/or to alter their shape, for example, to pass through an opening that is smaller than the diameter of the contrast agent.

In contrast to the elastic contrast agents described above, it may be desirable, in certain circumstances, to formulate contrast agents from substantially impermeable materials such as polymer materials, including, for example, polymethyl methacrylate. This would generally result in the formation of contrast agents which may be substantially impermeable and relatively inelastic and even brittle. In embodiments involving diagnostic imaging, for example, ultrasound, contrast media which comprise such vesicles with limited elasticity would generally not provide the desirable reflectivity nor the ability to adequately gain access to the lumen of the lymphatic vessel. However, by increasing the power output on ultrasound or by applying another energy source, the vesicle can be made to rupture, thereby causing acoustic emissions which can be detected by an ultrasound transducer, can be deformed in such a way as to gain access to the lumen of the lymph vessel, or alternatively, release its contents that can then gain access to the lumen of the lymph vessel. Further, the contents of the vesicle can have diagnostic or therapeutic function that can be released in an extravascular site of interest such as a tumor, a lymph node, or any normal or abnormal region of a patient.

In accordance with preferred embodiments of the present invention, the contrast agents utilized in the present invention are useful for diagnostic imaging, including, for example, X-ray, x-ray computed tomography (CT) imaging, including CT angiography (CTA) imaging, magnetic resonance (MR) imaging, magnetic resonance angiography (MRA), nuclear medicine, ultrasound (US) imaging, optical imaging, elastography, infrared imaging, microwave imaging, and the like.

For x-ray or computed tomography imaging, the contrast agent should have a different electron density than surrounding tissues (either more or less electron density) to render it visible with these techniques. With respect to contrast agents for CT, it is generally sought to employ agents that will increase electron density in certain areas of a region of the body (positive contrast agents). Suitable electron density is achieved, for example, in compounds with bromine, flourine or iodine moieties, and in materials comprising or including radiopaque metal atoms. With respect to contrast agents for CT, is also sought to employ agents that will decrease electron density in certain areas of a region of the body (negative contrast agents). Suitable agents can be fat or air or any substance with lower electron density than water.

For MRI, contrast agents which are suitable for use in accordance with invention methods should have adequate nuclear or relaxation properties or susceptibility effect for imaging that are different from the corresponding properties of the tissue being imaged. Either an imageable nucleus (such as $^{19}$F), radionuclides, diamagnetic, paramagnetic, ferromagnetic, superparamagnetic substances, and the like, can be used with appropriate MRI equipment.

Ultrasound and x-ray imaging, including the use of digital subtraction techniques, may also be utilized according to another embodiment of the present invention. Ultrasound contrast agents can be selected on the basis of density or acoustical properties. Preferably, the contrast agent is echogenic. As employed herein, the term "echogenic" refers to a contrast agent that may be capable of reflecting or emitting sound waves. Echogenic contrast agents may be particularly useful to alter, for example, the acoustic properties of a lymph tissue, organ or region of a patient, preferably the sentinel lymph node, thereby resulting in improved contrast in diagnostic imaging techniques, such as those described herein. As previously alluded to, microbubble preparations are particularly compatible with ultrasound imaging.

In this regard, any contrast agent that can be selectively rendered more detectable within a lymphatic structure by exposure to a particular treatment or energy may be employed in the present invention. Moreover, the selected contrast agent may be imaged using other than traditional detection procedures. For example, contrast agents that are traditionally used in conjunction with ultrasound detection methods (i.e., microbubble agents) may, in the context of the present invention, be used with magnetic resonance visualization methods. That is, the contrast agent may be imaged using ultrasonic energy and the infusion of intact, detectable contrast agents monitored through magnetic resonance. While any imaging agent possessing the requisite properties may be employed, preferred embodiments of the invention comprise the use of ultrasound contrast agents and/or magnetic resonance imaging. agents. For example, a preferred contrast agent may comprise a microbubble preparation wherein the microbubbles are associated with an MRI agent such as a paramagnetic material.

As indicated above, a number of contrast agents may be employed in the practice of the present invention, including droplets, bubbles, microbubbles, polymer particles, microspheres, microballoons, microcapsules, suspensions, emulsions, and the like. As discussed herein, particularly preferred embodiments of the present invention comprise the use of microbubble-based imaging agents. Accordingly, microbubble formulations suitable for use in the methods of the present invention are described in some detail below. However, it will be appreciated that the present methods are not limited, in any way, to the use of these particular microbubble formulations.

In one preferred embodiment, the contrast agents are adapted to return a signal at a frequency different from the frequency of the ultrasonic pulse emitted by the transducer, such as a harmonic frequency of the ultrasonic pulse. That is, the contrast agents are adapted for harmonic imaging such as is described in U.S. Pat. No. 5,540,909 which is incorporated herein by reference in its entirety. Yet, it must be emphasized that, while the present invention may often be described in the context of the preferred embodiments, the invention is not limited to the use of such formulations.

Contrast agents, and particularly microbubble contrast agents, contemplated for use in the present invention may be formulated, for example, from lipids, polymeric materials, proteins, and the like. The lipids, polymers, and/or proteins may be natural, synthetic or semi-synthetic. It should be noted that for medical uses, the selected contrast agent should be biocompatible or not be physiologically deleterious or injurious to biological functions, and which will not result in any degree of unacceptable toxicity, including allergenic responses and disease states. For example, ultimately, components comprising the contrast agent may decay wherein the components will preferably be released into the blood either as dissolved particles or gas or as submicron droplets of condensed liquid. It will be understood that gases will primarily be removed from the body through lung respiration or through a combination of respiration and other metabolic pathways including the reticuloendothelial system.

As previously indicated, microbubbles contemplated for use in the practice of the present invention are those that are free, or are surrounded or comprise an elastic or rigid shell, wall, or membrane. As employed herein, the term "shell" (used interchangeably with the terms, "wall" or "membrane") is used to refer to the material surrounding or defining a microbubble, whether it be a surfactant, another film forming liquid, a solid or semisolid outer layer, and the like. The walls may be concentric or otherwise. In a presently preferred microbubble, the shell is formulated from lipids (i.e., phospholipids), natural and synthetic polymeric materials, proteinaceous materials, carbohydrates, sacchirides, and the like. In addition, in presently preferred microbubbles, the shells may be in the form of a monolayer or bilayer, and the mono- or bilayer may be used to form one or more mono- or bilayers. In the case of more than one mono- or bilayer, the mono- or bilayers may be concentric, if desired. Preferably, lipids may be used to form a unilamellar microbubble (comprised of one monolayer or bilayer), an oligolamellar microbubble (comprised of about two or about three monolayers or bilayers) or a multilamellar microbubble (comprised of more than about three monolayers or bilayers). Similarly, the microbubbles prepared from polymers or proteins may comprise one or more walls or membranes, concentric or otherwise. The walls or membranes of microbubbles prepared from lipids, polymers, or proteins may be substantially solid (uniform), or they may be porous or semi-porous.

When referring to the pressure of dissolved gas in a liquid, the more familiar term "pressure" may be used interchangeably with "tension." "Gas osmotic pressure" is more fully defined below, but in a simple approximation can be thought of as the difference between the partial pressure of a gas inside a contrast agent and the pressure or tension of that gas (either in a gas phase or dissolved in a liquid phase) outside of the contrast agent, when the membrane is permeable to the gas. More precisely, it relates to differences in gas diffusion rates across a membrane.

It will be appreciated that the contrast agents utilized in the present methods should have a lifetime sufficient to enable them to persist for the time period during which images and/or measurements are taken. In accordance with preferred embodiments of the present invention, several ultrasound contrast agents that are commercially available or under development may be used to provide the desired images.

In this respect, suitable contrast agents include Imagent (AFO150), Alliance Pharmaceutical Corp., San Diego, Calif.; AI-700, Acusphere, Inc., Cambridge, Mass., AIP201 by UofV; Albunex and Optison (FS069), both by Molecular Biosystems, Inc., San Diego, Calif.; Echogen and QW7437 both by Sonus Pharmaceuticals Bothell, Wash.; Levovist (SH/TA-508), Echovist and Sonovist (SHU563), all by Schering AG, Berlin, Germany; Aerosomes-DMP115 and MRX115, by ImaRx Pharmaceuticals, Tucson, Ariz.; BR1 and BR14, both by Bracco International B.V., Amsterdam, NL; Quantison and Quantison Depot, both by Andaris, Ltd. Nottingham, GB; and NC100100, Nycomed Imaging AS, Oslo, Norway, and the like. Contrast agents and methods of forming contrast agents usable in the present invention are disclosed in U.S. Pat. Nos. 4,957,656, 5,141,738, 4,657,756, 5,558,094, 5,393,524, 5,558,854, 5,573,751, 5,558,853, 5,595,723, 5,558,855, 5,409,688, 5,567,413, 5,558,856, 5,556,610, 5,578,292, 5,271,928, 5,531,980 5,562,893, 5,837,221, 4,572,203, 4,844,882, 5,552,133, 5,536,489 and 5,558,092, each of which is incorporated herein by reference in its entirety. International applications WO 96/40282, WO 95/01187 and WO 96/40278 further describe compatible contrast agent preparations and are also incorporated herein. Additional suitable contrast agents, as well as their compatible characteristics are described, for example, in Calliada et al., Eur J Radio (1998) Suppl 2:S157–160, the disclosures of which are hereby incorporated herein by reference in their entirety.

The microbubble contrast agents employed in the methods of the present invention preferably contain a gas and/or vapor (or precursor thereof). When referring to a "gas," it will be understood that mixtures of gases together having the requisite properties fall within the definition, except where the context otherwise requires. A "vapor," on the other hand, is the gaseous phase of a material that is a liquid at ambient temperature and pressure, but that has an appreciable vapor pressure at the relevant temperature, e.g., body temperature. The gas and/or vapor may provide the contrast agent with enhanced imaging capabilities, such as reflectivity of ultrasound, particularly in connection with microbubble compositions in which the gas is entrapped within the microbubble. Those skilled in the art will appreciate that the term "gas" as used herein shall be held to mean gases, gas mixtures or vapors unless otherwise specified.

As suggested above, fluorocarbon or fluorinated gases or vapors are particularly preferred as osmotic or stabilizing agents for microbubble preparations. The term "fluorocarbon" is used herein in its broadest sense and includes fully fluorinated compounds (perfluorocarbons) as well as partially fluorinated hydrocarbon materials (fluorochemicals or fluorinated compounds), including unsubstituted chains or those substituted with another halogen such as Br, Cl, or I or another substituent, such as O, OH, S, NO, and the like. For example, sulfur hexafluoride would be considered a fluorocarbon gas for the purposes of the present invention and may be used to provide stabilized microbubble preparations in accordance with the teachings herein. In selected embodiments, microbubbles useful with the present invention may contain materials that can change state from a gas to a liquid or solid at body temperature, (generally from about 35.5° C. to about 40° C.), and at useful pressures (generally about 1–2 atm). Similarly, fluorocarbons or other compounds that are not gases at room or body temperature can be used, provided that they have sufficient vapor pressure, preferably at least about 10–20 Torr, and more preferably 30, 40, 50 or 100 Torr at body temperature, or more preferably at least about 150 or 200 Torr.

In particular, substances possessing suitable solubility and/or vapor pressure criteria for the formation and use of microbubbles in accordance with the invention include fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotriethylamines, and the like. Particularly preferred embodiments of the present invention employ microbubbles comprising perfluorohexanes, perfluoropentanes, perfluorobutanes, perfluoropropanes, sulfur hexafluoride, and the like. One particular preferable class of compatible compounds comprises flouroethers. Other useful gases or vapors comprise Freon 113, methylene chloride, Freon 12 (dichlorodifluoromethane), Freon 11 (trichloromonofluoromethane), butanes, pentanes, hexanes, propane, methane, ethane, and the like.

Whichever gases or osmotic agents are ultimately selected, it will be appreciated that microbubbles comprising mixtures of gases and/or vapors may be used with the disclosed methods as can microbubbles comprising pure gases. For example, both mixtures of fluorocarbon gases (i.e. fluorohexane and fluorobutane) and fluorocarbon gases mixed with nonfluorocarbon compounds (i.e. fluoropentane and nitrogen) can form particularly stable microbubbles. It will further be appreciated that several types of gas or vapor are compatible with either microbubble configuration, i.e. they are useful as a component of a mixture or in a pure state.

In this regard, mixtures of gases and/or vapors may be used to form particularly long lasting contrast agents. This is because contrast agents of a primary modifier gas such as air or nitrogen (including fluorocarbon gases) saturated with a selected perfluorocarbon osmotic agent can grow rather than shrink when exposed to air dissolved in a liquid due to the osmotic pressure exerted by the perfluorocarbon gas or vapor. Preferably, the osmotic agent is relatively impermeable to the contrast agent film and thus remains inside the contrast agent. Air or other gases inside the contrast agent are diluted by the perfluorocarbon, which acts to slow the air diffusion flux out of the contrast agent. This gas osmotic pressure is proportional to the concentration gradient of the perfluorocarbon vapor across the contrast agent film, the concentration of air surrounding the contrast agent, and the ratio of the contrast agent film permeability to air and to perfluorocarbon.

Further, as disclosed in U.S. Pat. No. 5,315,997, gases and perfluorocarbon vapors have magnetic susceptibilities substantially different from tissues and blood. Therefore, microbubble contrast agents comprising fluorinated compounds will cause changes in the local magnetic fields present in tissues and blood during MRI. As such, the aforementioned microbubble contrast agents may also be used for magnetic resonance visualization. Other exemplary MRI agents, which may be used with the present invention comprise paramagnetic and supraparamagnetic macromolecular compounds or particulates that may be associated with microbubbles (i.e. on the membrane) or mixed with a microbubble contrast agent. Examples of such imaging agents are to be found in U.S. Pat. Nos. 4,675,173 and 4,849,210, each of which is incorporated herein by reference. With respect to paramagnetic compounds, gadolinium diethylenetriaminepentaacetic acid (Gd-DTPA), and transition metal ions of iron and manganese may be used in conjunction with the disclosed invention, particularly when attached to a larger molecule such as human serum albumin, dextran or polylysine. Regarding supraparamagnetic imaging agents, those comprising iron oxides may be used to provide perfusion data with the disclosed methods.

It will be appreciated that those of ordinary skill in the art can readily determine other compounds that would perform suitably that do not meet both the solubility and vapor pressure criteria, described above. Rather, it will be understood that certain compounds can be considered outside the preferred range in either solubility or vapor pressure, if such compounds compensate for the aberration in the other category and provide a superior insolubility in water or high vapor pressure or affinity to dissolve in the surfactant used.

It will further be understood that other components can be associated with useful contrast agent formulations. For example, osmotic agents and stabilizers (described herein), chelators, surfactants, buffers, viscosity modulators, air solubility modifiers, salts, sugars, and the like, can be added to fine tune the contrast agent suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation. Such components associated with useful contrast agents can be in addition to, or instead of the materials (lipids, polymer, protein, gas, vapor, liquid, and the like, described herein) which comprise the contrast agent. In addition, these components can be associated inside, on or outside the contrast agent. Thus, with respect to microbubbles, such components can be within the void, part of the shell or membrane, or part of the solution which surrounds the microbubble.

In a preferred embodiment of the present invention, the lymphatic tissues retain contrast agents of the invention for an extended period of time. Long retention time may allow the use of these contrast agents for therapy of the lymphatic tissues, particularly when using the diagnostic and biologically active or therapeutic substances of this invention releasing a therapeutic agent in the site of accumulation. Therefore, if desired, the contrast agent described herein may further comprise a targeting agent to alter the biodistribution of an agent, to increase its concentration in a desirable lymphatic structure, and/or to decrease its concentration in non-target sites, thereby suppressing side effects and/or diffusion. To provide accumulation of a contrast agent in a lymph site, molecules possessing a high affinity to target tissue are preferably used as target agents. Antibodies or their fragments, and receptor ligands (e.g., hormones, cytokines or their analogues) are common examples of high affinity molecules employable as target agents.

In accordance with a preferred embodiment of the present invention, the contrast agent comprises targeting agents or modifications to increase uptake and accretion of the contrast agent by the first lymph node (sentinel lymph node) where they will be removed by endothelial or phagocytic cells. For example, target agents which can be included in useful contrast agents include a radiocolloid-type agent which is scavenged by the reticuloendothelial system (RES) and accretes the contrast agent in lymphatic structures beyond the sentinel lymph node, e.g., chemically modifying the contrast agent to promote macrophage uptake by attachment of a macrophage receptor substrate. The targeting agent may also be a radiolabeled lipid or agent such as gallium citrate, labeled bleomycin, or the like, which accretes in lymphatics. In preferred embodiments, these agents will be associated with a microbubble agent. In addition, and advantageously for certain cases, it may be a new type of imaging agent developed especially for this invention, namely, a radiolabeled antibody which specifically binds to normal lymphatic tissues or cells, but not to tumors or lesions located therein or proximal to and draining into the structure, so that it is also diffusely distributed in the lymph nodes and reveals the internal structure thereof.

Various combinations of the materials comprising or surrounding the contrast agents may be used to modify the relaxation behavior of the medium or to alter properties such as the viscosity, osmolarity, stability, sterility, isotonicity, biocompatibility, imageability, brightness, and the like. For example, the gas and vapor filled contrast agents used in the present invention may be controlled according to size, solubility and heat stability by choosing from among the various additional or auxiliary stabilizing materials described herein. These materials can affect these parameters of the contrast agents, especially contrast agents formulated from lipids, not only by their physical interaction with the membranes, but also by their ability to modify the viscosity and surface tension of the surface of the gas and gaseous precursor filled vesicle.

Accordingly, the gas and gaseous precursor filled contrast agents contemplated for use in the present invention may be favorably modified and further stabilized, for example, by the addition of one or more of a wide variety of (a) viscosity modifiers, including, for example, carbohydrates and their phosphorylated and sulfonated derivatives; polyethers, preferably with molecular weight ranges between about 400 and about 100,000; di- and trihydroxy alkanes and their polymers, preferably with molecular weight ranges between about 200 and about 50,000; and the like; (b) emulsifying and/or solubilizing agents including, for example, acacia, cholesterol, diethanolamine, glyceryl monostearate, lanolin alcohols, lecithin, mono- and di-glycerides, monoethanolamine, oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan monooleate, sorbitan mono-palmitate, sorbitan monostearate, stearic acid, trolamine, emulsifying wax, and the like; (c) suspending and/or viscosity-increasing agents, including, for example, acacia, agar, alginic acid, aluminum monostearate, bentonite, magma, carbomer 934P, carboxymethylcellulose, calcium and sodium (and/or sodium 12), carrageenan, cellulose, dextran, gelatin, guar gum, locust bean gum, veegum, hydroxyethyl cellulose, hydroxypropyl methylcellulose, magnesium-aluminum-silicate, Zeolites(r), methylcellulose, pectin, polyethylene oxide, povidone, propylene glycol alginate, silicon dioxide, sodium alginate, tragacanth, xanthan gum, alpha-d-gluconolactone, glycerol, mannitol, and the like; (d) synthetic suspending agents, such as polyethylene glycol (PEG), polyvinylpyrrolidone (PVP), polyvinyl alcohol (PVA), polypropylene glycol (PPG), polysorbate, and the like; (e) tonicity raising agents which stabilize and add tonicity, including, for example, sorbitol, mannitol, trehalose, sucrose, propylene glycol, glycerol, and the like; and other similar materials.

As previously indicated, the contrast agent can be used alone, or in combination with additional diagnostic, therapeutic or other agents. Such other agents include excipients such as coloring materials. As employed herein, the term "diagnostic agents" refers to detectable agents, in addition to or other than the contrast agents described herein, useful in diagnostic methods, e.g., MR agents, CT agents, ultrasound agents, optical imaging agents, dyes, and the like. As employed herein, the term "bioactive agents" refers to biologically active agents, e.g., therapeutic compounds. In this respect it will be appreciated that compatible bioactive agents may be selected from the group consisting of analgesics, antibiotics, leukotriene inhibitors or antagonists, antihistamines, antiinflammatories, antineoplastics, anticholinergics, anesthetics, enzymes, steroids, genetic material, viral vectors, antisense agents, proteins, peptides, and the like, and combinations thereof.

For optical imaging, optically active gases, such as argon or neon, may be incorporated in the present compositions. In addition, optically active materials, for example, fluorescent materials, including porphyrin derivatives, may also be used. Elastography is an imaging technique which generally employs much lower frequency sound, for example, about 60 KHz, as compared to ultrasound (which can involve frequencies of over about 1 MHz). In elastography, the sound energy is generally applied to the tissue and the elasticity of the tissue may then be determined. The lipid based vesicles described herein are preferably highly elastic, and they may increase the local elasticity of tissue to which they are directed. This increased elasticity may then be detected with elastography. If desired, elastography can be used in conjunction with other imaging techniques, such as MRI and ultrasound.

In a preferred embodiment of the present invention, the contrast agent will comprise a labeling substance, such as a blue dye or a minute amount of radioactively labeled tracer substance. Preferably, the labeling substance is carried within the contrast agent, such as a microbubble, and released when the contrast agent reaches the sentinel lymph node, i.e., by disruption of the contrast agent employing ultrasound. The blue dye and the radioactive tracer are used because the "sentinel node" is not always easy to find. Through a small incision in the axilla the surgeon can pick out the node (sometimes there are 2 or 3) that turns blue with the dye and/or emits a radioactive particle which is then detected with a probe like a Geiger counter.

Contrast Agent Formation

Methods for the preparation of contrast agents contemplated for use in the present invention will be readily apparent to those skilled in the art, once armed with the present disclosure, especially when the present disclosure is coupled with information known in the art, such as that described in Unger, U.S. Pat. No. 5,846,517, the disclosure of which is hereby incorporated herein by reference in its entirety.

There are a variety of procedures which can be used to prepare contrast agents for use with the disclosed methods, including, for example, shaking, microemulsification, vortexing, extrusion, filtration, sonication, homogenization, repeated freezing and thawing cycles, extrusion under pressure through pores of defined size, and similar methods known to those skilled in the art. For example, a microbubble preparation may be formed by reducing the pressure on a flourocarbon-in-water emulsion. Rehydration of spray dried hollow microspheres to form microbubbles is preferred. Sonication is also a preferred method for the formation of contrast agents, i.e., through an ultrasound transmitting septum or by penetrating a septum with an ultrasound probe including an ultrasonically vibrating hypodermic needle. However, it will be appreciated that a variety of other techniques exist for contrast agent formation. For example, gas injection techniques can be used, such as venturi gas injection.

Other methods for forming contrast agents include formation of particulate microspheres through the ultrasonication of albumin or other protein as described in European Patent Application 0,359,246; the use of tensides and viscosity increasing agents as described in U.S. Pat. No. 4,446,442; the use of lipid coated, non-liposomal, contrast agents as described in U.S. Pat. No. 4,684,479; the use of liposomes having entrapped gases as described in U.S. Pat. Nos. 5,088,499 and 5,123,414; and the use of denatured albumin particulate microspheres as described in U.S. Pat. No. 4,718,433. Each of these contrast agent compositions is suitable for use with the methods of the present invention and, accordingly, the foregoing patents and applications are hereby incorporated by reference herein in their entirety.

Administration of Contrast Agents

Any of the above described contrast agent for imaging lymphatic structures of interest may be administered to a vertebrate subject, such as a bird or a mammal. As employed herein, the term "lymphatic structure" refers to cells, tissues or organs which comprise or are associated with the lymph system, including lymph nodes, lymph vessels, lymph canals, lymph cells, macrophages, injection situs, and the like. Preferably, the vertebrate is a human, and the lymph structure of interest, such as the lymph nodes, lymph vessels, and the like, can be imaged with any of the techniques described herein. This can be useful, e.g., for detecting the lymph nodes, tumors, necrotic regions, and infected regions.

In accordance with a preferred embodiment of the present invention, there are provided methods for identifying the sentinel lymph node associated with tissues or organs which are neoplastic (or presumed neoplastic), infectious, and the like. The present invention also allows for the diagnosis or detection of defects or irregularities in lymph nodes. Major areas of interest for imaging of the sentinel lymph node include regional spread of neoplastic and infectious lesions of the breast, colon and rectum, prostate, ovary, testes, skin cancer, and the like. Major lymph nodes involved in these various lesions include axillary and internal mammary nodes in the chest, and the pararectal, anterior pelvic (obturator), internal iliac (hypogastric), presacral, external and common iliac, and para-aortic nodes. Thus, applications where lymphographic imaging would be useful include, but are not limited to, pathological lesions affecting the major organs of the chest, abdomen and pelvis, as well as the skin, from which the regional and, subsequently, more distant lymphatics can be involved.

It will be appreciated that lymphatic structures of interest can be imaged employing different modes of visualization, including direct lymphangiography, indirect lymphography, lymph scintigraphy, MR lymphography, and the like. The different modes of visualization are known in the art, as well as suitable modes of administration of contrast agents, are discussed, for example, in Vogl et al. (*Acta Radiol.* (1997) Supp 412:47–50), the disclosure of which is hereby incorporated by reference in its entirety.

As those skilled in the art would recognize, administration of the contrast agents described herein, as well as the auxiliary materials, can be carried out in various fashions which are not intravascular, including parenteral. Parenteral administration, which is preferred, includes administration by the following routes: intramuscular, percutaneous, directly in the lymphatic vessel or the lymph node, intraepidermal, intramedullary, intramural or intraparenchymal, interstitially, intraperitoneal, intrathecal, subcutaneous, intrasynovial, transepithelial (including transdermal), dermal, in the tumor or pathologic process itself, and the like. Preferably, the contrast agent is administered by interstitial injection (or other interstitial administration) in the vicinity of the lymph node to be imaged, including subcutaneous (under or in the skin) and intraparenchymal (into an organ) injection, but not intraperitoneal injection (into a body cavity). In the case of cancer patients, the contrast agent is preferably injected in proximity to the cancer. The contrast agent can also be injected by a combination of two or more parenteral modes, for example intramuscular, subcutaneous, and in the pathologic process, insuring its accretion in the lymphatic structure of interest. Upon administration, the contrast agent is preferably taken up by the lymphatic system, generally localizing in lymph nodes (preferably the sentinel lymph node) afferent to the uptake site. Thus, preferably, the contrast agent would follow the same route as a metastatic tumor cell would be likely to follow within the lymphatic system.

Suspensions or formulations comprising contrast agents are administered in a manner compatible with the route of administration, the dosage formulation, and in a diagnostic effective amount. It is anticipated that dosages between about 0.1 to about 30 ml of the agent (about 10 micrograms up to about 1 milligram per kilogram of body weight) per day will be used for diagnostic applications. In accordance with a preferred embodiment of the present invention, a small quantity of the contrast agent (e.g., about 0.1 ml/Kg based on the body weight of the vertebrate) is introduced into the animal per injection site, but this can vary depending on the site and the number of injections. Other quantities of the contrast agent, such as from about 0.005 ml/Kg to about 1.0 ml/Kg, are also contemplated for use in the practice of the present invention. Volumes of the contrast agent will normally vary somewhat depending upon the site of injection, the concentration and activity of the preparation, the number of injections to be used, the particular contrast agent employed, the characteristics of the lymphatic structure desired, the degree and duration of effect desired, the judgment of the practitioner, as well as properties peculiar to each individual. Moreover, suitable dosage ranges for systemic application depend on the route of administration. In addition, it will be appreciated that the image of the lymphatic structure will vary depending on the contrast agent employed (e.g., depending upon their half-lives, their sensitivity to the ultrasound or other energy employed, their imaging characteristics, i.e., energy ranges, emission intensities, scatter, and the like, the stability of the contrast agent, especially antibody conjugates, their rate of transport to the lymph nodes, their distribution and clearance, the time at which imaging is to be done, and the like), the auxiliary or stabilizing material and/or suitable carrier, the lymph structure, the injection site, and the like. Adjustment of these parameters will be conventional for the ordinary skilled clinician. Suitable regimes for initial administration are variable, but are typified by an initial administration followed by repeated doses at one or more intervals.

In addition, the contrast agent may be in the form of a sterile injectable suspension or formulation comprising contrast agents combined with suitable carriers. Suitable carriers include non-toxic parenterally-acceptable sterile aqueous or nonaqueous solutions, suspensions, or emulsions, including the auxiliary or stabilizing materials, surfactants, and the like (each which have been described herein). This suspension may be formulated according to known methods using suitable dispersing or wetting agents and suspending agents, including the auxiliary or stabilizing materials described herein. They can also be manufactured in the form of sterile water, or some other sterile injectable medium immediately before use. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. They may be sterilized, for example, by filtration through a bacteria-retaining filter, by incorporating sterilizing agents into the formulations, by irradiating the formulations, by heating the formulations, and the like. Sterile injectable suspensions may also contain adjuvants such as preserving, wetting, emulsifying, and dispersing agents. Buffers, preservatives, antioxidants, and the like can also be incorporated as required.

The imaging agent will normally be administered at a site and by means that insure that it is mobilized and taken up into the lymphatic circulation. This will vary with the system to be imaged. Multiple injection sites may be preferable in order to permit proper drainage to the regional lymph nodes under investigation. In some cases, injections around the circumference of a tumor or biopsy site is desired. In other cases, injection into a particular sheath or fossa is preferred. Injection into the webs of the fingers or toes is a common mode used to study peripheral lymphatics. The contrast agent can be administered to the subject either pre-operatively and/or intra-operatively to localize the sentinel lymph node. It is recognized that the present invention, preferably, allows immediate and real-time identification of the lymph vessel and the sentinel draining node following percutaneous injection of the contrast agent in a region of interest. Administration of the contrast agent does not require significant lead time to reach the nodes. In addition, additional methodology can be employed to modify or alter the transport of the contrast agent to the lymph structure, including massaging the injection site or stimulating flow by exercise to facilitate transport of the contrast agent to the lymphatic structure of interest. Preferably, the site of injection of the contrast contrast agent will be massaged to promote uptake of the contrast agent by the lymph vessel to spontaneously and on demand fill the lymph vessel and the draining lymph node.

The invention method can be used to visualize iliopelvic lymphatics in genitourinary cancers. For example, to visualize the sentinel lymph node associated with genitourinary cancers or lesions, bilateral deep perianal injection of the contrast agent into the ischiorectal fossa is effective. For example, the patient can be placed in the lithotomy position and about 1 ml of the contrast agent is introduced bilaterally into the ischiorectal fossa, e.g., with a 22 gauge needle, to a depth of about 1.5 inches just lateral to the anal margin, at the 9 and 3 o'clock positions. The patient may also lie on the side if achieving the lithotomy position is not possible. Subcutaneous dorsal pedal injection of about 0.5 ml of the contrast agent may also be made, e.g., using a 23 gauge half-inch needle in the first interdigital spaces bilaterally.

In certain cases, such as testicular or prostatic cancer or some cases of rectal carcinoma, intratumoral or peritumoral injection of imaging agents can be effective.

The present method also has applicability in locating the sentinel node associated with breast tumor. Images of axillary, subclavian and supraclavicular nodes may be obtained by injecting the contrast agent into and around the tumor and below the skin adjacent to the tumor or the medial surface of the upper arms (ipsilateral and contralateral) of patients with breast cancer. A unilateral injection can be made in the subcostal site ipsilateral to the tumor, and then repeated later on the contralateral side to observe cross drainage between the ipsilateral and contralateral nodes. Alternatively, for example, for visualization of the internal mammary lymphatics in breast cancer, the contrast agent is injected into the posterior rectus sheath at the insertion of the diaphragm in the subcostal site, using about 1 ml of the contrast agent. By injecting a contrast agent in the vicinity of the tumor, the practitioner will know that the lymph duct involved and leading to the sentinel node will be directed toward the axillary, internal mammary, or supraclavicular chain wherein imaging is effected at appropriate times after each injection.

Another approach is to inject about 0.5 to 1 ml of contrast agent around the areola tissue of the breasts bilaterally, and then imaging the axillary, internal mammary, or supraclavicular chains. In addition to periareolar injection, interdigital administration of the contrast agent may be used for visualization of axillary lymphatics (see, DeLand et al., (1980), Cancer Res. 40:2997–3001). Combined interdigital and periareolar administration of the contrast agent can provide increased accuracy to demonstrate increased uptake in affected axillary nodes. Intratumoral injection of the contrast agent can also be performed in patients with breast cancer or melanoma and is a useful mode of administration for certain cases.

Preferably, the contrast agents persist for a sufficient amount of time following administration to allow measurements of the rate of increase in contrast agent levels in the target region and the determination of maximum signal strength. In this respect preferred imaging agents have a half life of at least about 1 minute following administration. More preferably the imaging agents have a half life of at least about 2, 3, 5, 10 or 30 minutes or more following administration. However, those skilled in the art will appreciate that the disclosed invention may be practiced by continuous administration of an imaging agent having any half life including those with half lives on the order of seconds or tens of seconds.

In accordance with yet another embodiment of the present invention, the sentinel node is then removed for evaluation as to the presence or absence of neoplastic or infectious diseases or disorders, including metastasis. Thus, the diagnostic procedure is minimally invasive, as other non-affected regional axillary nodes are not disturbed. When compared with the conventional surgical protocols of removing essentially all regional lymph nodes at the axilla, the minimally invasive aspect of the present methodology immediately becomes apparent.

Imaging Techniques

In accordance with the present invention, any imaging techniques which allow for the monitoring of the infusion of contrast agent into the target region are compatible with the teachings herein. In this regard, all forms of imaging techniques are contemplated in the present invention, including, for example, imaging by X-ray, computed tomography (CT) imaging, including CT angiography (CTA) imaging, magnetic resonance (MR) imaging, magnetic resonance angiography (MRA), nuclear medicine, ultrasound (US) imaging, optical imaging or spectroscopy, elastography, infrared imaging, microwave imaging, and the like. Moreover, the imaging may be combined to provide multiple exposures of the contrast agent following administration. The imaging techniques that are employed are known in the art, and these techniques are described generally in Kopans, D. B. Md., Breast Imaging (Lippincott-Raven Publishers 1998), the disclosure of which is incorporated by reference herein in its entirety.

Computed tomography (CT) is a valuable diagnostic imaging technique for studying various areas of the body. This technique measures the radiodensity (electron density) of matter. CT imaging techniques which are employed are conventional and are described, for example, in Computed Body Tomography, Lee, J. K. T., Sagel, S. S., and Stanley, R. J., eds., 1983, Ravens Press, New York, N.Y., especially the first two chapters thereof entitled "Physical Principles and Instrumentation", and Scroggin, Lippincotts Computer Tomography Review (Lippincott-Raven Publishers 1995), the disclosures of which are incorporated by reference herein in their entirety.

Magnetic resonance imaging (MRI) is another diagnostic imaging technique which may be used for producing images of the body in a variety of scanning planes such as, for example, axial, coronal, sagittal or orthogonal. MRI employs a magnetic field, radio frequency energy and magnetic field gradients to make images of the body. Similar to CTs, the magnetic resonance imaging techniques which are employed are conventional and are described, for example, in D. M. Kean and M. A. Smith, Magnetic Resonance Imaging: Principles and Applications, (William and Wilkins, Baltimore 1986), and in Rajan, S. S., MRI: A Conceptual Overview (Springer Verlag 1997), the disclosures of which are incorporated by reference herein in their entirety. Contemplated MRI techniques include, but are not limited to, nuclear magnetic resonance (NMR), electronic spin resonance (ESR), and the like. The presently preferred imaging modality is NMR imaging.

With respect to ultrasound, ultrasonic imaging techniques contemplated for use in the present invention are well known in the art, and are described, for example, in McGahan and Goldberg, Diagnostic Ultrasound: A Logical Approach (Lippincott-Raven Publishers 1998), and in Frederick and Kremkau, Diagnostic Ultrasound: Principles and Instruments, (W B Saunders Co. 1998), the disclosures of which are hereby incorporated herein by reference in their entirety. Specific ultrasound imaging modes useful with the disclosed invention include harmonic or non-linear imaging, grey scale (B-mode), Doppler (including pulsed wave, Power, flow, color, amplitude, spectral and harmonic), 3-D imaging, gated imaging, and the like. With respect to harmonic imaging, it will be appreciated that the present invention is compatible with wideband harmonic imaging and pulse inversion harmonic imaging. Those skilled in the art will further appreciate that any of these imaging modes may be used to provide the signal levels which, upon processing, can afford the desired values for fluid flow rates and fluid content.

If one desires to use harmonic imaging (an optional embodiment of the present invention), and the ultrasound imaging machine is set to image at a particular frequency, the outgoing waveform supplied to the sonic transducer can be a numerical fraction of the imaging frequency (e.g., ½, ⅔, ⅓, and the like) or a whole number or fractional multiple of the imaging frequency (e.g., 2, 3/2, 3, 4, and the like). With any particular combination of contrast agents and excitation frequency, certain harmonics will be dominant. The second harmonic is a common example. Those strongest harmonics are preferred for obvious reasons, although other harmonics or frequencies may be selected for reasons such as preparation of multiple images or elimination of background. Moreover several frequencies, including harmonic and non-harmonic frequencies or some combination thereof, may be simultaneously detected to provide the desired image. That is, in preferred embodiments any frequency other than the interrogation frequency may be used to provide the desired data. Of course, those skilled in the art will appreciate that dominant harmonics can be determined by simple empirical testing of the contrast agent preparation.

To detect the reradiated ultrasound energy generated by the contrast agents, a modified conventional ultrasound scanner system or commercially available harmonic imaging systems can be used. These systems are able to detect or select one or more or all of the new frequencies, or harmonics, radiated by the contrast agents for production of the ultrasound image. In other words, it detects a frequency different from the emitted frequency. Equipment suitable for harmonic ultrasound imaging is disclosed in Williams et al., WO 91/15999. Many conventional ultrasound imaging devices, however, utilize transducers capable of broad bandwidth operation, and the outgoing waveform sent to the transducer is software controlled. For this reason, reprogramming to emit a waveform different from the one detected is well within the level of skill in the art.

Although harmonic ultrasound imaging is particularly preferred for use in the disclosed methods and systems, other types of ultrasound imaging such as B-mode (gray scale imaging), F-mode (color flow or Doppler imaging) and D-mode (spectral Doppler) are also compatible and within the purview of the instant invention.

In B-mode imaging, the ultrasound system typically transmits a series of beams, along scan lines, steered to scan a desired field of view. The ultrasound system typically steers "receive beams" in a manner that corresponds to the transmit beams. Data returned from each receive beam is communicated to an image display subsystem which reconstructs a two-dimensional gray scale image from the B-mode data and displays it on a console. Such series of pulses down a single line may be identical or may be of equal or unequal frequency or have a near 180 degree phase shift (inverted pulse) to promote the distinction of the contrast agent from the surrounding tissues.

F-mode imaging is accomplished in a manner similar to B-mode imaging, in that the ultrasound system fires and receives a series of beams to scan a field of view. However, since F-mode imaging requires calculation of the velocity of targets, each line is fired and received several times. As with B-mode imaging, the data returned from each firing of each line is used to reconstruct an image on a console.

F-mode imaging is often used concurrently with B-mode imaging. For example, the gray scale image reconstructed from a B-mode scan can be superimposed with an F-mode image reconstructed from an F-mode scan of the same field of view or of a lesser included field of view. The F-mode information can be displayed using colors, with different colors indicating different positive or negative flow velocities or turbulence at the part of the B-mode image on which the pixel is superimposed. Because F-mode imaging is intended to provide only qualitative insight into target motion in the patient's body, the ultrasound system's processing of F-mode signals need not have high spatial or velocity resolution either in amplitude or in pixel resolution.

However, since an important value of F-mode imaging is to detect flows relative to anatomical structures in the body, it is usually important that the F-mode image be properly registered with the B-mode image on-screen. Since this technique relies on the correlation of signal obtained from one pulse versus the subsequent pulse, and since vesicles can be destroyed by the first pulse, an F-signal is generated that is not related to motion. This loss of correlation can be shown in a variety of display formats but is typically displayed in color.

In D-mode (spectral Doppler) acquisition, the ultrasound system fires a beam and processes the return signal for a single target. Spectral Doppler information can be obtained by transmitting and receiving either continuous wave (CW) or pulsed wave (PW) ultrasonic energy. In CW Doppler acquisition, for example, Power Doppler (Doppler angiography), the ultrasound receiver continuously receives echoes from all objects within the receiver's area of sensitivity in the body, and cannot isolate information received from any specific range interval. CW Doppler is most useful where the instrument's area of sensitivity can be adjusted, either by physical placement of the probe or by beamforming, or both, to include only the desired target. In PW Doppler acquisition, the ultrasound instrument receives echoes from individual pulses, the timing of which implies a range interval within the body of the object which produced the echo. A clinician typically selects a range interval within which the target is expected to be located.

In D-mode acquisition, it is desirable to be able to produce detailed quantitative measurements over a very large range of signal levels (dynamic range). D-mode information is processed by the ultrasound system to display either the velocity spectrum of the target, plotted against time, or to provide an audio output carrying similar information. Spectral Doppler acquisition is described in Liv Hatle, M.D. & Bjorn Angelsen, Dr. Techn., "Doppler Ultrasound in Cardiology" (1st ed. 1982) and (2d ed. 1984), incorporated herein by reference in its entirety.

In addition to B-, F- and D-mode acquisition, a fourth mode also exists, known as M-mode, but this is merely a different display modality for data acquired in a manner similar to B- or F-mode acquisition. The requirements for M-mode acquisition are not significantly different from those for B- or F-mode acquisition. Alternatively, or in addition, 3-dimensional ultrasound is also contemplated, wherein 3-D scans require special probes and software to accumulate and render the images.

Additional diagnostic techniques contemplated for use in the present invention are well known in the art, and are described, for example, in Gamsu et al., Diagnostic Imaging Review (W B Saunders Co 1998), the disclosure of which are incorporated by reference herein in its entirety.

In the case of diagnostic applications (such as ultrasound, CT, MRI, and the like), energy, such as ultrasonic energy, may be applied to at least a portion of the patient to image the target tissue. A visible image of an internal region of the patient, preferably the lymphatic structure, may be then obtained, such that the identification of the sentinel lymph node can be ascertained. Of course, it will be appreciated that the same images could be used to detect or diagnose defects or irregularities in the lymphatic structure.

All U.S. and Foreign Patent publications, textbooks, and journal publications referred to herein are hereby expressly incorporated by reference in their entirety. The invention will now be described in greater detail by reference to the following non-limiting examples.

EXAMPLES

The invention was put in practice using a rabbit model with a Vx2 tumor implanted by bolus injection in the calf. The popliteal fossa was imaged with a Siemens Sonoline Elegra scanner equiped with a 7 MHz trasnducer and the enlarged lymph nodes identified. 0.5 mL of AF0150 (Alliance Pharmaceutical Corp.) was injected at the margin of the leg tumor nearest the popliteal fossa and another 0.5 ml injected in the foot pad of the affected leg using a 23G needle. The popliteal lymph nodes were imaged with standard, wideband, and burst wideband sonography immediately after injection and during massage of the foot pad. The lymph vessel leading to the popliteal node could be recognized as an echogenic line leading to the node. This process could be repeated several times. The lymph node fed by this vessel was enhanced and complete filling was achieved with intermittent imaging with a delay of 5 to 10 seconds. The delay time required to fill the node increased as the experiment progressed over the following minutes. The enhancement of the node was best appreciated with wideband harmonic imaging.

While the invention has been described in detail with reference to certain preferred embodiments thereof, it will be understood that modifications and variations are within the spirit and scope of that which is described and claimed.

That which is claimed is:

1. A method for diagnosing a lymphatic disorder of one or more lymph structures in a subject, said method comprising:

administering in the region of one or more lymph structures of said subject a diagnostically effective amount of a particulate ultrasound contrast agent, said contrast agent having a mean particle size in the range of about 1 micron up to about 10 microns in diameter, wherein said contrast agent is administered subcutaneously or intramuscularly such that at least a portion of said contrast agent enters the lymphatic circulation of the subject;

imaging said subject using ultrasound whereby at least one regional lymph structure is detected on the image by measuring said contrast agent in the lymphatic circulation, and detecting the lymphatic disorder by comparing the image of the at least one regional lymph structure with that of a normal lymph structure.

2. A method according to claim 1, wherein said contrast agent is administered so as to localize in or pass through the lymphatic circulation.

3. A method according to claim 2, wherein said method further comprises massaging the site of administration or stimulating the site of administration by exercise or by applying ultrasound.

4. A method according to claim 1, wherein said particulate contrast agent comprises a microbubble preparation having dispersed therein a plurality of microbubbles.

5. A method according to claim 4, wherein said microbubbles comprise a fluorocarbon gas or gas precursor.

6. A method according to claim 1, wherein said ultrasound imaging comprises harmonic ultrasound imaging.

7. A method according to claim 1, wherein said contrast agent carries a labeling substance that is released at any site from the point of administration to any portion of a lymphatic chain.

8. A method according to claim 1, wherein said contrast agent carries a therapeutic substance to treat or effect a target tissue at the site of administration or anywhere along the lymphatic circulation.

9. A method according to claim 1, wherein the at least one lymph structure is downstream from tissue that is neoplastic or suspected to be neoplastic.

10. A method according to claim 1, wherein said contrast agent is modified to promote macrophage uptake.

11. The method of claim 1, wherein the lymphatic disorder is selected from a lymphatic metastasis of cancer, a lymphoma, and a lymph node hyperplasia.

12. The method of claim 7, wherein the contrast agent is activated or made to release its contents into the lymphatic circulation by applying an external energy.

13. The method of claim 12, wherein the external energy is mechanical or ultrasonic.

14. A method for detecting a sentinel lymph node in a subject, said method comprising:

administering to tumor-bearing tissue of said subject a diagnostically effective amount of a particulate ultrasound contrast agent comprising a plurality of microbubbles having a mean particle size in the range of about 1 micron up to about 10 microns in diameter, wherein the contrast agent is administered intramuscularly, subcutaneously, dermally, transdermally, intraepidermally or intraparenchymally and wherein at least a portion of the contrast agent passes from the site of administration to enter into the lymphatic circulation of the subject; and imaging said subject using ultrasound so as to detect the lymph node nearest the tumor in the tumor bearing tissue.

15. A method according to claim 14, wherein said plurality of microbubbles comprise a fluorocarbon gas or gas precursor.

* * * * *